(12) United States Patent
Cordova

(10) Patent No.: US 6,380,300 B1
(45) Date of Patent: Apr. 30, 2002

(54) PROPENAMIDE BASED COOLING GEL PLAY COMPOSITION

(75) Inventor: Abimael Cordova, Whittier, CA (US)

(73) Assignee: Mattel, Inc., El Segundo, CA (US)

( * ) Notice: Subject to any disclaimer, the term of this patent is extended or adjusted under 35 U.S.C. 154(b) by 0 days.

(21) Appl. No.: 09/503,605

(22) Filed: Feb. 11, 2000

(51) Int. Cl.⁷ .............................................. C08L 39/00
(52) U.S. Cl. ...................................................... 524/555
(58) Field of Search ......................................... 524/555

(56) References Cited

U.S. PATENT DOCUMENTS

| | | | |
|---|---|---|---|
| 4,586,288 A | * 5/1986 | Walton | 47/73 |
| 4,769,414 A | 9/1988 | Kightlinger et al. | 525/54.24 |
| 4,925,603 A | 5/1990 | Nambu | 264/28 |
| 5,502,967 A | 4/1996 | Nakagawa et al. | 62/3.3 |
| 5,503,583 A | 4/1996 | Hippely et al. | 446/14 |
| 5,837,029 A | * 11/1998 | Behel | 71/63 |

* cited by examiner

Primary Examiner—Paul R. Michl
(74) Attorney, Agent, or Firm—Robert W. Mulcahy

(57) ABSTRACT

The invention is directed to a coolant gel composition containing propenamide polymers, a paraben-based preservative, and water in certain amounts to form a composition having gel strength, elasticity, and cold retention properties to enable the gel to function as a color variation inducing material for low temperature thermochromic materials. The nature of the instant cooling gel renders it suitable for use in a hand operated color variation inducing device in the toy field.

15 Claims, 3 Drawing Sheets

PROPENAMIDE BASED COOLING GEL PLAY COMPOSITION

TECHNICAL FIELD OF THE INVENTION

The present invention relates to a composition of matter and process for preparation of a propenamide based gel which is used as a cooling medium in a color variation inducing device capable of inducing color variation in toy articles bearing thermochromic materials.

BACKGROUND OF THE INVENTION

Toys using thermochromic or light sensitive materials embedded or mixed in plastic printed on paper or plastic, or impregnated in fibers used for clothing, doll hair or the like are all very well known. In U.S. Pat. Nos. 4,917,643 and 5,503,583 there are disclosed dolls and toy vehicles containing surface coatings of thermochromic materials which change color upon a child's application of warm or cold water. In still other applications going back in time, in U.S. Pat. No. 3,382,607 (May 14, 1968) a toy figure having synthetic hair fibers impregnated with an indictor dye which changes color in response to contact with liquids of varying pH levels. While a host of color changing toy devices and mechanisms (e.g. thermochromic) are known, very few means or devices have been proposed to actuate a color change in a thermochromic environment by contact with a heating or cooling source.

In Laid open Japanese Utility Model Application No 62-139573 there is disclosed the concept of bringing an electrical heating utensil, equipped with a heating resistor such as of tungsten or nickel, into contact with a thermally color varying material formed on the surface of an animal toy or the like, thereby inducing a color variation in the contacted are a. In U.S. Pat. No. 5,502,967 to Nakagawa et al. there is disclosed a variable hot/cold electrothermal device which can be positioned in contact with a thermally color varying surface area, thereby inducing color variation in the contacted zone. This patented device, while effective, is electrically sophisticated and, accordingly, is expensive and impractical for exploitation by young children in connection with a toy. Moreover, the device is outfitted with heating elements which will doubtlessly pose safety problems with any prospective use in the toy industry. For practical economic and safety purposes, any toy articles bearing thermochromic materials generally must rely on household water temperatures or ice cooling systems for actuation of the color variation in such articles.

The present invention is directed to a cooling gel composition and its use in a simple toy contact device. Color variations in household articles containing thermochromic materials by cooling means has generally required the use of cold water or ice pieces, or by keeping the thermally color varying article in a refrigerator. Such cooling means to induce color variation in thermochromic material may be applicable in certain specified places such as in the home, but are not generally usable elsewhere. Therefore, this cooling media, being limited in duration of a required low temperature (coldness), requires a cumbersome operation each time of use. Moreover, the thermally color varying articles are generally not water resistant and, consequently, are often deteriorated by water drops resulting from direct contact with the cooling medium (e.g. ice) or from leaking of a container housing the acqueous cooling medium.

In developing a cooling gel and color variation induction device herein, it has remained imperative that the gel materials be safe for young children. Safety requirement have evolved through the years as safety concerns have grown. Generally, safety requirement mandate that play material compositions be nonirritating to the skin or eyes or the like, and be nontoxic if ingested. Additional requirements have been expected of these materials to avoid damage to clothing, upholstery fabric, or carpeting.

Cooling gels are known for use in cooling media and are otherwise known as chilling gels, coldness-keeping gels, coldness -keeping heat transfer medium, colloidal coolant, coolant composition of ice pillow. However, these known coolant gels are generally not satisfactory for toy use because they are generally cryogens (freezing mixtures) having (i) high heat absorbancy, rendering them useful as refrigerant gels in portable containers, and (ii) are generally composed of chemicals, including freeze lowering additives, both of which characteristics are incompatible and/or unsafe for toy use.

The present invention is directed to a gel composition comprised of homopolymers and copolymers or crosslinked homopolymers and copolymers of 2-propenenitrile and 2-methyl-2-propenenitrile. Gel compositions are aqueous compositions generally thickened with gums, starches, resins, fine silica or other water absorbants. The instant polymeric materials are excellent water absorbents and it has been found that they form firm, strong gels having excellent cold retention and heat absorbency properties comparable or equal to ice (water) or ice cream but more enduring and steady in cold retention (melting rate) Accordingly, the instant gels are acceptable for toy use in that they have the required child safety features in terms of the gel materials and contact heat loss from a frozen or cold form of these gels. Additionally, these absorbent polymers can be cleaned up and removed from carpets and fabrics with water should they escape from a contemplated container.

SUMMARY OF THE INVENTION

The present invention is based on the discovery that homopolymers an copolymers or crosslinked homopolymers and copolymers of 2-propenenitrile and 2-methyl-2-propenenitrile have superior water absorbent properties to form firm gels having good thermodynamic properties in terems of high cold retention properties enabling the material to function as a cooling gel medium, particularly suited for toy use. These polymers additionally possess a non-toxic character and are water miscible thereby rendering them usable as, or in, toy devices. The invention comprises a novel gel composition, its use in a color variation inducing device, and processes for making and using the gel composition. The gel composition is comprised of water, homopolymers and copolymers of 2-propenenitrile and 2-methyl-2-propenenitrile and a significant amount of a preservative comprising alkyl parabens. The gel can be used as a cooling medium which is firm, strong, highly flexible and elastic, and provides a comfortable touch. The gel peels and fragments so that it may be packed in a container for coolant gel use. Further the gel may be molded to have a desired shape and dimensions and immediately used as a final product without the need of a shaping operation.

In accordance with the present invention, there is provided a strong, elastic, non-toxic cooling gel composition which has a firm gelatin character, a comfortable touch and moistened feeling. The gel is comprised of (i) at least 90% by weight of water, (ii) an absorbent comprised of saponified polymers or copolymers of 2-propene-nitrile and 2-methyl-2-propenenitrile in a lesser amount than water, and (iii) still lesser amounts of a preservative selected from the group of alkyl parabens consisting essentially of methyl, ethyl, propyl, and butyl parabens (p-hydroxy benzoate) and mixtures thereof. A preferred absorbent used herein is the corlymer poly(2-propenamide-co-2-propenoic acid, the sodium salt). The present gels are child user friendly and cold retentive because they can be cooled at temperatures of from about below freezing temperatures (freezer cooling) up to 45° F. (refrigerator cooling) and retain such lower temperatures over hours of time. It is this feature in combination with low temperature thermochromic dyes which can be exploited by children to induce color variation n countless toy items.

The instant cooling gel composition is employed in a color variation inducing device which in combination with a color-varying system enables applications to various fields including toys. The instant device provides a casing or housing for encasing and supporting the instant cooling gel, said casing being in the form of an elongated cylindrical applicator having a lateral wall defining a circumferential shaft for gripping, around the device. The device is rendered functional by cooling the gel filled application to temperatures of at least as low as 32° F. to 40° F. and applying it to a low temperature thermochromatic or color varying containing surface. The cooling) gel-filled applicator can be employed with toys containing thermochromic dyes or pigments to produce a variety of patterns, designs, numbers, letters, or other indicia which change color as the temperature of the thermochromic containing surfaces of the toys varies.

In one preferred form, a cooling gel composition is comprised of (i) at least 90% by weight of an aqueous portion; (ii) at least 3 weight percent of an absorbent comprised of saponified polymers or copolymers of 2-propenenitrile and 2-methyl-2-propenenitrile; and (iii) at least 1% by weight of an alkyl paraben preservative selected for the group of consisting essentially of methyl, ethyl, benzyl, and propyl parabens (p-hydroxy benzoate) and mixtures thereof. The composition further may optionally includes appropriate small amounts of humectants, plasticizers, fragrances or gel colorants depending on the toy application of the gel contemplated.

The present toy play gel composition is prepared by:
a) mixing water and an alkyl paraben preservative selected for the group of consisting essentially of aryl-alkanols, methyl, ethyl, propyl, and butyl parabens (p-hydroxy benzoate) and mixtures thereof to form an aqueous solution and water at an elevated temperature, to form a solution; and
b) concurrently adding and mixing an absorbent comprised of polymers or copolymers of 2-propenenitrile and 2-methyl-2-propenenitrile until a strong, firm gelatin is formed.

DETAILED DESCRIPTION OF THE INVENTION

Figure 1:
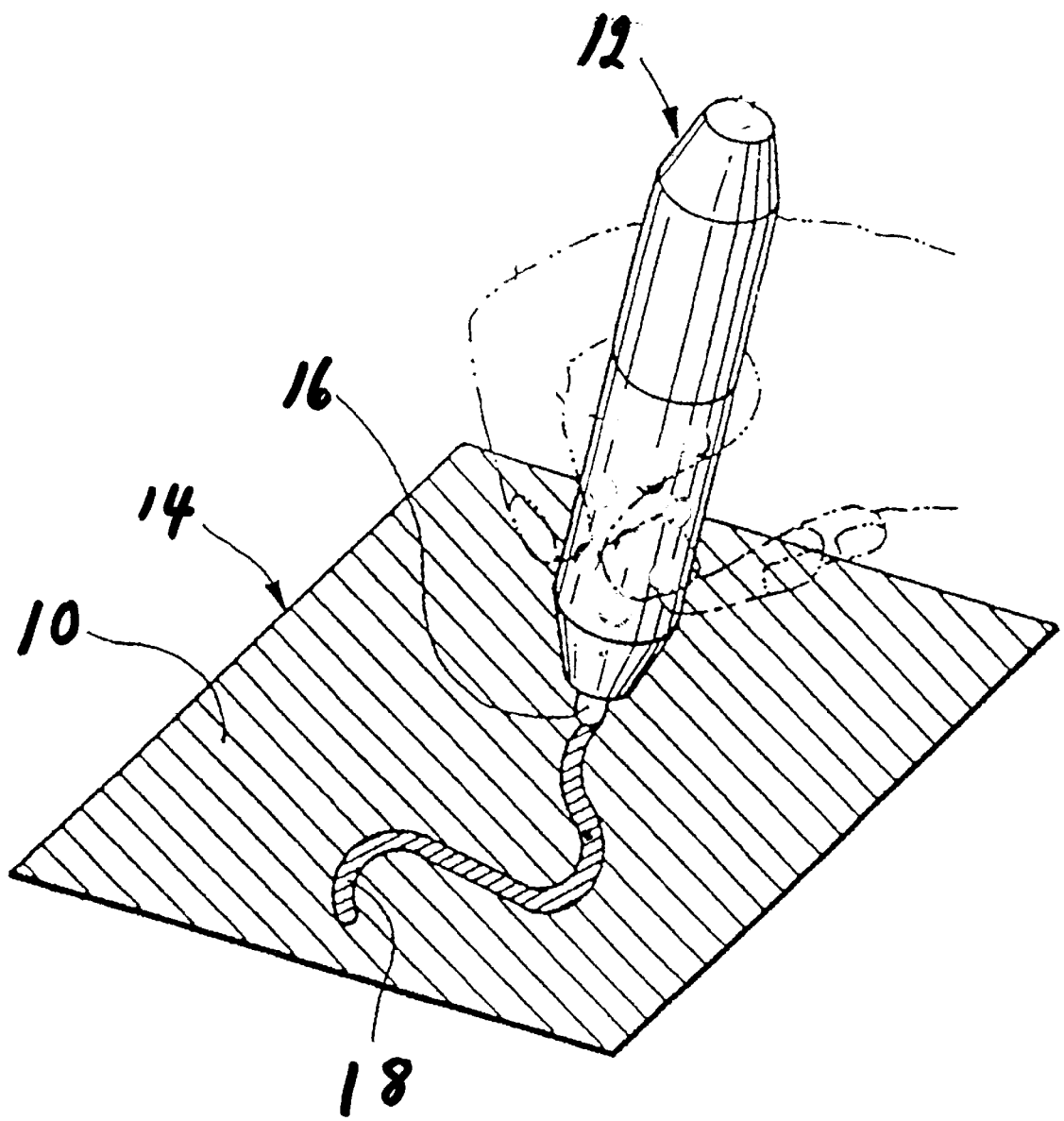
FIG. 1 is a schematic view of one application embodiment of a color variation inducing device according to the subject invention.

The cooling gel composition of the present invention recognizes the creation of a casting or molded gel composition for use as coolant medium because of its good hermodynamic properties, which is strong and highly elastic, free of unpleasant odor, and provide a comfortable touch and moist feeling. The present coolant gel has a high water content but can be readily reversibly cooled or frozen when placed in a refrigerator cabin or freezer or other household freezing environment. In accordance with the invention, there is presented a cooling gel composition comprising (i) water; (i) binder in the form of polymers or copolymers of 2-propenenitrile and 2-methyl-2-propenenitrile in their saponified, salt, or crosslinked form; and (ii) alkyl paraben preservative selected from the group of consisting essentially of methyl, ethyl, benzyl, and propyl parabens (p-hydroxy benzoate) and mixtures thereof. The gel composition has the aforementioned strength and elastic characteristics as well as a steady and enduring heat absorbency (or cold retention). The composition can further comprise other well known optional ingredients such as binder additives, colorants, fragrances, or plasticizers to facilitate different applications in the toy or other arts.

A process for preparing the instant the steps of (i) mixing the parabens and water at room temperatures to from an aqueous solution; and then (ii) concurrently adding and mixing the absorbent propenamide with the aqueous paraben solution wherein there commences formation of a gel having the already cited excellent thermodynamic and mechanical properties. The preparation of the present coolant gels does not involve any additional pretreatment or after treatment, i.e. secondary hardening steps, the use of an acid, alkali, radical sources, irradiation, organic solvents, or other solvents than water, many of which have been necessary in pre-treatment or gelation steps of the prior art high polymer gels. Nonetheless, the gel obtainable by the process of this invention contains water in a high content and has rubber-like elasticity and sufficient structural or mechanical strengths suited for use as a cooling medium or coolant gel, especially in the application of these gels in combination with low temperature thermochromic colorants in the toy or entertainment industries.

The absorbent polymers and copolymers of 2-propenenitrile a d 2-methyl-2-propenenitrile used herein have: the properties of high absorbancy, such as those exhibited by silica gels at high humidity; quick gelling and high gel strength attributes; ready availablity and a relatively low cost; and compatibility with most water based binders such as vinyl acetate based copolymers. Additionally the instant propenamide absorbent polymers are safe for domestic use, as in toys, in that these polymers can be used as suspending agents and adhesive additives in food products. These polymers and copolymers may be prepared in accordance with processes outlined in U.S. Pat. No. 4,796,414 (issued Sep. 6, 1988) owned by Grain Processing Corporation and herby incorporated by reference. A particularly preferred polymer or copolymer of 2-propenenitrile and 2-methyl-2-propenenitrile in the purview of this invention is the saponified copolymer of poly(2-propenamide-co-2-propenoic acid) (the sodium salt thereof.) The preparation of an aqueous solution of the instant polymers and c polymers of 2-propenenitrile and 2-methyl-2-propenenitrile involves adding the binder polymer to an aqueous solution of the paraben preservatives at room temperature. Although the concentration of these polymers and copolymers is not critical, when the aqueous solution contains only these polymers (and no other binder), the concentration of these polymers and copolymers may range from about 0.5 to 5% by weight and preferably from 2 to 4% by weight of the total gel composition. Although the concentration of these absorbent polymers and copolymers in the aqueous solution may be raised, the solution will exceed 10,000 cP (Centipoints) at ambient temperatures, with increasing viscosity resulting in undesirable precipitous gelation. For these reasons, the concentration of polymers and copolymers of 2-propenenitrile and 2-methyl-2-propenenitrile in the aqueous paraben preservative solution should not be so high as to encounter difficulties in handling.

In the preparation process herein, certain paraben based preservatives are added to the initial aqueous solution of the instant polymers and copolymers of 2-propenenitrile and 2-methyl-2-propenenitrile. The particular parabens are selected from the group of alkyl parabens consisting essentially of methyl, ethyl, benzyl, and propyl parabens (p-hydroxy benzoate) and mixtures thereof. The parabens should be in an overall concentration of from about 0.5 to weight percent of the total gel composition. These paraben based preservatives can have small amounts of alcohol such as 2-phenoxyethanol in their compositional formulation to facilitate solution of the organic parabens. For example, the preservative known as Phenonip contains a mixture of methyl, ethyl, propyl, and butyl p-hydroxybenzoates dissolved in 2-phenoxyethanol. The alcohol additive is inconsequential to the gel and serves no function because of its relatively small amounts in the total composition of the gel.

It has been found that this group of perservatives has a unique structure which enables the alkylated p-hydroxy benzoate molecules to inter-react with the absorbent binder polymers and copolymers of 2-propenenitrile and 2-methyl-2-propenenitrile so as to capture, immobilize, and contain any otherwise loose water molecules. While not to be construed a limiting, it is therorized that the relatively high concentration of parabens to absorbent molecules enables the paraben molecule to crosslink the absorbent propenamide molecules and alter (increase) the water absorbtion rate of propenamide so as to result in fast and strong water gelation. This phenomena explains the exceptional thermodynamic and mechanical properties of the present cooling gel. It should be noted here that the discovered unexpected and synergistic combination of the polymers and copolymers of 2-propenenitrile and 2-methyl-2-propenenitrile with the alkyl parabens is unique to the instant invention. In sum, the instant coolant gel composition is the combination of the cited several ingredients which synergistically provide or the desirable properties of the instant gel invention recited above.

A suitable pigment or dye is optionally employed in the present strong elastic cooling gel composition to color the gel itself and enhance its effect in a toy item. Without the pigment or dye, the composition is basically translucent, while with up to 6% by weight of a suitable pigment or dye the play material can be made to take on an array of vivid colors. Typical pigments and colorants include synthetic organic colorants sold as the T-series by the Day Glow Corporation of South Gate City, Calif. Other pigments which can be used include sodium aluminum sulpho silicate sold as MR 582 by the Cleveland Pigment Corp. of Cleveland, Ohio; polyamide condensates with organic dyes with less than 2% phthalocyanine; tetra-chloro-zincate sold by the Day Glow Corporation: and. FD&C Powder Series colorants sold and distrbuted by Warner & Jenkinson.

It is important that the instant coolant gel based composition remain comfortable to the touch and generate a moistened feeling throughout its effective life. To achieve this goal, small amounts of humectants or plasitczer may be added to prevent the loss of water to any extent so the user may reconstitute the mass to is original character merely by wetting ones hands. Humectants frequently employed in gel compositions include glycerine, polyglycols including glycerol, and/or polypropylene glycol, and Carbowax. The humectants employed herein equally function as plastercizers thereby promoting elongation (stretch) of the gel which may undesirably reduce the strength of the instant coolant gel. Additionally, humectants such as glycols can reduce the freezing point of the gel which in undesirable for the instantly contemplated toy gel application. Accordingly, the humectants should be used in very small quantity as needed to achieved the desired results for this gel invention.

In the preferred embodiments of the present invention, the proportionate parts of the instant pliable play gel material are as follows:

TABLE I

| Ingredient | Percent by Weight |
|---|---|
| Water | 80.00–98.00 |
| Absorbant Binder (propenenitrile polymers) | 1.0–20.00 |
| Colorant | 0.0005–1.00 (as needed) |
| Paraben Based Preservatives | 0.50–3.00 |
| Plasticizer (Humectant) | As needed |
| Fragrance | As needed |

As indicated, a preferred embodiment of the present cooling gel invention adds fragrance or plasticizer materials as needed. The fragrance material is added solely to enhance the fragrance of the formulation and no maximum or minimum weight of fragrance material is set forth in Table I. Of course, the percentages of these main ingredients will change as fragrances, humectants, or plasicizers are added or increased. It will be recognized by those killed in the art that the colorant and fragrance ingredients may be varied or omitted without departing from the spirit and scope of the present invention.

Table II sets forth an exemplary embodiment of the present play gel material

TABLE II

| Ingredient | Percent by Weight |
|---|---|
| Deionized Water | 94.0% |
| Superabsorbant G-400 Binder | 4.5% |
| Colorant | 0.000 (as needed) |
| Preservative (P-Hydroxy-benzoate mixture) | 1.5% |
| Fragrances | 0.00 (as needed) |
| Humectant (Glycerol) | 0.00 (as needed) |

The absorbant/binder, Superabsorbant G-400, is the saponified copolymer of poly(2-propenamide-co-2-propenoic acid, sodium salt) and is available from the Grain Processing Co of Iowa. The preservative is Phenonip, a mixture of parabens (alkyl P-Hydroxy-benzoate) and 2-phenoxyethanol available from Nipa Laboratories, Inc. of Wilminton, Del. It should be appreciated from the detail of Table II that the water, the propenenitrile polymer binder, and the alkyl P-Hydroxy-benzoate preservative mixture are the only essential elements to achieve instant strong,elastic cooling gel having the cold retentive and comfortable touch and moistened tactile feel characteristics necessary to the instant composition invention. Also shown in Table II are colorant (pigments or dyes) and humectant additives and an ingredient referred to as "fragrance" all of which are generally present in preferred fabrications of the instant cooling gel composition but are not necessary items to achieve the advantageous gel characteristics.

More specifically and with reference to Table II, the absorbant binder (or thickener) portion of the present invention is comprised of a propenenitrile polymer selected from the group consisting essentially of saponified polymers or copolymers or starch graft copolymers of of 2-propenenitrile and 2-methyl-2-propenenitrile and is present in a compositional range of from about 2.00 to 8.00 weight percent of the total composition. An especially preferred absorbant for this group is the saponified copolymer of poly(2-propenamide-co-2-propenoic acid) (the sodium salt thereof.). It is to be appreciated the binder portion of the formulation may include a soluble cellulose additive such as Klucel HF (water soluble hydroxypropyl cellulose) manufactured by the Aqualon Company present in amounts of up to 2.5 weight percent. Other cellulose binder additives include hydroxy-methyl cellulose sold by Dow Corning under the trademark "Methocel", hydroxy-benzo cellulose sold as "Benzozel" by Aqualon Co., and hydroxy-propyl-methyl cellulose sold as "Prima Flow" by the Hercules Chemical Co.

Deionized water is present at slightly less than 98% and is acceptable ill percentages of between about 80% to 98% by weight of the total composition. Phenonip, a preservative, can be used at concentration of between about 0.5 to 5% by weight and preferably between concentrations of between about 1 to 2% by weight and is very effective with the present absorbent binders due to the product's content comprised of a mixture of alkyl p-hydoxy-benzoates.

The instant invention includes a process for producing the composition includes mixing the preferred paraben preservatives with water and then adding with concurrent mixing the preferred absorbant, the copolymer of poly(2-propenamide-co-2-propenoic acid, the sodium salt), to form a suspension and allowing the instant strong elastic gel to form. The paraben containing Phenonip preservative is excellent and can be used in the initial aqueous solution along with a colorant generally at room temperature or cooler, all contained in a "Cowles" mixer main tank. The absorbent binder is then added to the aqueous/paraben solution with mixing and can be then poured into a cast or molding and allowed to set, thereby allowing the gel to congeal into a strong elastic gelatin structure in the shape of the mold or cast.

Turning now to FIG. 1, there is demonstrated a color variation induction system for inducing color variation in a thermally color-varying layer 10 by positioning the color variation inducing device 12 in contact with or in the proximity of a thermally color varying article 14 comprised of a color varying layer 10 of a low temperature thermochromic material. A cold transition member 16 is provided at the application point of the color inducing (device 12 and is preferably composed of a metal, but other materials such as a thin member of rubber, plastic or ceramic can be used. A magnetic metal cold transition member may also b employed for attraction to a metal or otherwise magnetized color varying article. The cold transmitting member 16 can be formed as a writing or coating tip, a stamp, or a circular or polygonal shape according to the application, or as a toy or entertainment element such as a comb for a doll, a make up article, or any other appropriate item for other toy color changing applications.

The color variation inducing device 12 shown in FIG. 1 is in the form of an elongated cylindrical article having a coolant filled chamber (shown is FIG. 2) and a circumferential exterior housing functioning as a shaft, thereby facilitating hand gripping as shown as a background hand grip in FIG. 1. The chamber (see FIG. 2) is filled with the propenamide coolant gels of the instant invention. The thermally color varying article 14 consists of a white sheet the entire surface of which is coated a color varying layer comprised of a low temperature thermochromic dye, pigment, or other material with a lower color varying point of 35° C. and a higher color varying point of 55° C. The color variation inducing device 12 is placed under refrigeration and cooled to 35° C. and the cold tip 16 applied to the to the thermochromically coated color varing surface (being white at room temperature) where a black inscripted line 18 is drawn with the writing tip 16.

Figure 2:
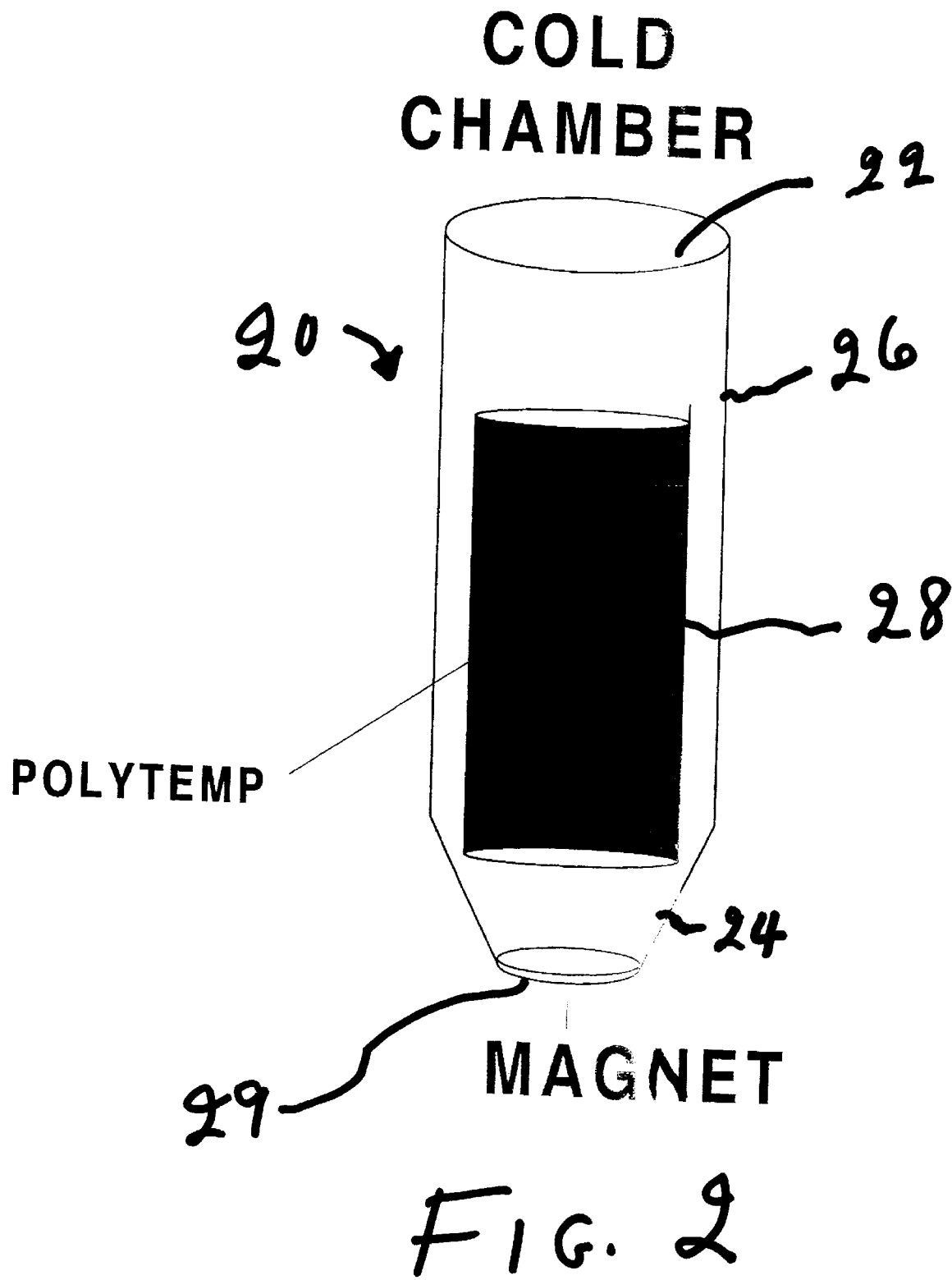
FIG. 2 is a cross-sectional view of one structural embodiment of a color variation inducing device according to the subject invention.

Turning to FIG. 2, there is shown an upright cross sectional view of the instant color variation inducting device 20 which is comprised of a hollow chamber 22 drawn to a tapered conical end section 24 for application focus of this cold inducing contact apparatus. The hollow chamber 22 is form of a circumferential outer surface casing or housing 26 which supports and houses the instant propenamide coolant gel invention shown as 28. The device further comprises a metal magnet 29 in the form of a thin circular coin or plate which piece will in addition to generating magnetic attraction, be a heat application transmission member (shown as item 16 of FIG. 1) and operable in the demonstrated construction or, alternatively, may function as a contact element for a further cold transmission element piece (not shown) in the form of a functional shape for application to a low temperature thermochromic medium (e.g. a comb structure for a doll's thermochromic hair). The casing 26 may be formed from any functional plastic such as ABS (acetyl butadiene-styrene copolyomers), polycarbonates, high density polypropylene etc.

Figure 3:
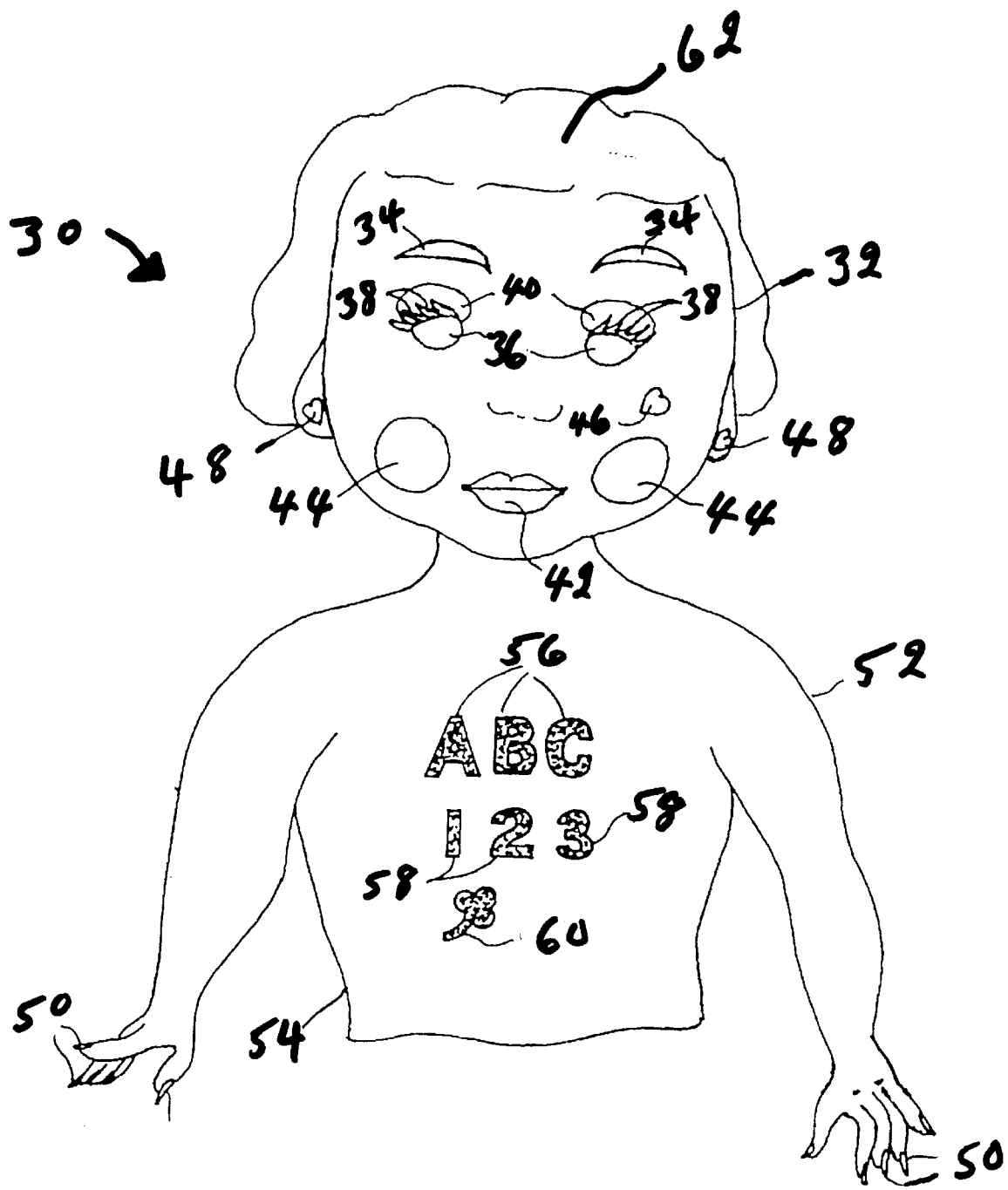
FIG. 3 is a schematic view of another application embodiment of the present invention in the form of a front elevational view of a toy doll having different portions thereof painted, coated or embedded with thermochromic material.

FIG. 3 demonstrates another application embodiment of the present invention in the form of a toy doll 30 having a head 32 and other portions thereof painted or embedded with low thermochromatic materials such as the doll's eyebrows 34, eyes 36, eye lashes 38, eyeshadow areas 40 above the eyes, lips 42, the dolls cheeks 44 and heartshaped beauty mark 46 on her face, and heart shaped earrings 48 on the doll's ears. Other portions of the doll 30 may be coated, painted or embedded with low temperature thermochromic material such as the finger nails 50 or toenails (not shown). Also other portions of the doll 30 may be similarly the thermochromically treated such as any portion of the arms 52, torso 54, legs (not shown) or any other part of the doll. As shown by way of example, the torso 54 may have tattoo items representing letters 56, numbers 58, designs and countless other low temperature thermochromatic configurations in or on the doll 30 as low temperature thermochromatic dye in the doll's hair 62.

Since these applied colorants to the doll 30 are low temperature thermochromic colorants (dyes or pigments), a child would subject the instant color variation inducing device (item 12 in FIG. 1 and item 20 of FIG. 2) to refrigeration at temperatures above 32° F. and apply the cold transmission member conical point (item 16 of FIG. 1 and item 29 of FIG. 2) to the various portion of the doll having low temperature thermochromatic colorants ebedded in or painted theron, thereby lowering the temperature of the thermochromatic materials and consequently causing the color of the applied are to change. The child may allow the affected areas of the doll such as the fingernails 50 to return to room temperature and enjoy the change back to the original color. Then the child may repeat the cold application with the instant color variation inducing device in the same sitting without further refrigeration of the propenamide coolant gel containing color variation inducing device because of the high cold retention character of the instant collant gel. The child may use a brush or comb attachment to the cold transmission elements 29 of FIG. 2 or 16 of FIG.

1 and comb the doll's thermochromatic hair and enjoy numerous hair color changes over several hours. Additionally, the thermochromic patches shown here may be coated on metallic or magnetically attractive backings and so will attract a magnetically tipped color variation inducing device of FIG. 2 (see item 29 of FIG. 2).

Any suitable thermochromic materials may be used within the purview of the instant invention such as those disclosed in U.S. Pat. No. 4,028,118 (Jun. 7, 1977) and U.S. Pat. No. 4,421,560 (Dec. 20, 1983) both of which are hereby incorporated by reference. Other materials that change color in response to temperature changes may also be used in the instant invention as, for example, the reversible heat sensitive recording composition disclosed in U.S. Pat. No. 4,720, 301 to Kito (Jan. 19, 1988), the disclosure of which is hereby incorporated by reference and are deemed "thermochromic materials". As such, "thermochromic material" as used herein is intended to refer to any suitable material that changes color in response to temperature variations.

It is to be understood that variations of the respective percentages of components set forth in Table II as being "preferred" may be undertaken without departing from the spirit and scope of the present invention. The important aspect of the invention is the use of (i) a majority amount by weight of water, and minor amounts of (ii) absorbent propenamide polymers selected from the group consisting of polymers and copolymers of 2-propenenitrile and 2-methyl-2-propenenitrile and (iii) preservatives selected for the group of alkyl parabens consisting essentially of methyl, ethyl, benzyl, butyl and propyl parabens (p-hydroxy benzoate) and mixture thereof. The resulting coolant gel material may be utilized in accordance with a variety of play patterns and applications involving children or adults as indicated above.

For purposes herein, there can be employed a thermochromic material containing a known thermochromic dye, such as a liquid crystal or a three-component system as described in U.S. Pat. Nos. 4,028,118 and 4,732,810. Also there can be employed a system based on a thermally color varying material, containing a color memorizing thermochromic dye, showing a large hysteresis, when the temperature is lowered from the high temperature side to the low temperature color varying temperatures contemplated for the thermochromatic material usable in the instant color varying inducing device. The thermochromatic dyes used herein are usually included in microcapsules and dispersed in a medium containing binder, in the form of ink or paint which is them applied to a toy item such as shown in FIG. 3. However any form of thermochromic material application is contemplated within the purview of the present invention. A full treatment of application of thermochromic material to toy is disclose in U.S. Pat. No. 5,503,583, the full disclosure of which is hereby incorporated by reference.

While particular embodiments of the invention have been shown and described, it will be obvious to those skilled in the art that other changes and modifications may be made without departing from the spirit and scope of the invention.

That which is claimed is:

1. An aqueous coolant gel comprising:
   i) water in an amount of at least 90% by weight;
   ii) an absorbent binder selected from the group of propenamide polymers selected from the group consisting of polymers and copolymers of 2-propenenitrile and 2-methyl-2-propenenitrile; and
   iii) an alkyl paraben preservative;
   said gel being characterized by high strength, elasticity, and thermodynamic properties enabling the gel to steadily maintain lower temperatures over relatively long periods of time.

2. The aqueous coolant gel of claim 1 wherein the preservative is selected from the group of parabens consisting essentially of methyl, ethyl, benzyl, butyl and propyl paraben (p-hydroxy benzoate), and mixtures thereof.

3. The aqueous cooling gel of claim 2 wherein the propenamide polymer is present in an amount of from about 0.5 to 5.0 percent by weight of the total combined weight of the gel composition.

4. The aqueous cooling gel of claim 2 wherein the paraben preservative is present in an amount of from about 0.5 to 3.0 weight percent of the total combined weight of the gel composition.

5. The aqueous cooling gel of claim 2 further comprising small amounts of a colorant, a fragrance material and a plasticizer.

6. The aqueous cooling gel of claim 2 wherein the propenamide polymer is the copolymer of poly(2-propenamide-co-2-propenoic acid).

7. The aqueous cooling gel of claim 1 wherein the propenamide polymer binder further includes hydroxy methyl cellulose, hydroxy propyl cellulose, hydroxy propyl-methyl cellulose, and hydroxy benzyl cellulose.

8. A aqueous cooling gel comprising the following materials expressed as percent by weight of the total composition:

| Ingredient | Percent by Weight |
|---|---|
| Water | 80.00–98.00 |
| Absorbant Binder (propenenitrile polymers) | 1.0–5.00 |
| Colorant | 0.0005–1.00 (as needed) |
| Paraben Preservatives | 0.50–3.00 |
| Plasticizer (Humectant) | As needed |
| Fragrance | As needed. |

9. A process for preparing a strong elastic cooling gel comprising:
   a) mixing sufficient amounts of a paraben preservative with water to firm a solution, said paraben preservative selected from the group of alkyl parabens consisting essentially of methyl, ethyl, benzyl, butyl and propyl parabens and mixtures thereof;
   b) concurrently adding and mixing an absorbent binder selected from the group of propenamide polymers selected from the group consisting of polymers and copolymers of 2-propenenitrile and 2-methyl-2-propenenitrile at room temperature to form a gel suspension; and
   c) allowing the suspension to set at room temperature until a strong elastic gel is formed.

10. The process of claim 9 wherein the pH of the suspension is maintained from about 6.0 to 8.7 during the gel formation step.

11. The process of claim 9 wherein fragrances, colorants, and plasticizers are added in small amounts prior to the final gel formation step.

12. The process of claim 9 wherein a binder additive compound selected from the group consisting essentially of hydroxy methyl cellulose, hydroxy propyl cellulose, hydroxy propyl-methyl cellulose, and hydroxy benzyl cellulose is added to the aqueous paraben solution in addition to the added absorbent propenamide polymers.

13. A color variation inducing device comprising:
   a) a housing or casing having a cylindrical shape, said casing having a lateral wall defining a circumferential hand gripping area circumscribing a chamber for supporting an aqueous coolant gel comprising an absorbent binder selected from the group of propenamide polymers consisting of polymers and copolymers of 2-propenenitrile and 2-methyl-2-propenenitrile; and b) a conical cold transmission element affixed to one end of the cylindrical casing and in thermal contact with the gel housing chamber to function as a probe contact point for the device;

wherein said coolant gel is rendered functional by application of temperatures of from below or equal to 32° F. to 45° F. to effect cooling of the conical point thereby rendering the device capable of inducing color variation in a low temperature thermochromic surface to which the conical cold transmitting point is contacted.

14. The color variation device of claim 13 wherein the propenamide polymer is the co-polymer of poly(2-propenamide-co-2-propenoic acid.

15. The color variation device of claim 13, formed as cold contact utensil in which the casing is a shaft and a contact cold transmission tip is provided in communication with both the conical contact point and the coolant gel housed in the casing.

* * * * *